United States Patent [19]

Foster

[11] Patent Number: 4,602,098

[45] Date of Patent: Jul. 22, 1986

[54] PROCESS FOR SEPARATION OF TOCOPHEROL HOMOLOGUES (I)

[75] Inventor: Charles H. Foster, Kingsport, Tenn.

[73] Assignee: Eastman Kodak Company, Rochester, N.Y.

[21] Appl. No.: 736,905

[22] Filed: May 22, 1985

[51] Int. Cl.$^4$ .......................................... C07D 311/72
[52] U.S. Cl. .................................................. 549/413
[58] Field of Search ............................... 549/413, 410

[56] References Cited

U.S. PATENT DOCUMENTS 2,350,713  6/1944  Baxter ................................. 549/413
4,480,108 10/1984  Foster ................................. 549/413

Primary Examiner—Nicky Chan
Attorney, Agent, or Firm—Clyde L. Tootle; J. Frederick Thomsen

[57] ABSTRACT

A process for separating the α-tocopherol homologues from the other ester members of a tocopherol homologue mixture. The isolation of the α-tocopherol homologue is accomplished by selective deacylation of a mixture of tocopheryl esters followed by separation of the α-ester from the other free tocopherols.

6 Claims, No Drawings

PROCESS FOR SEPARATION OF TOCOPHEROL HOMOLOGUES (I)

DESCRIPTION

This invention relates to a process for separating the various tocopherol homologues from mixtures of the tocopherol homologues. The isolation of the various tocopherol homologues is accomplished by selective deacylation of all tocopheryl esters except the α-homologue followed by the separation of the α-homologue esters from the free tocopherols.

Heretofore, various processes have been used for separating and isolating the various tocopherol homologues, for example, α-tocopherol. One previous method for separating and isolating the various homologues has been accomplished by ion exchange chromatography. However, because of the very small differences in structure of the various tocopherol homologues, these separation processes require large quantities of adsorbent or resins. Also, these processes are useful mainly only for isolating δ-tocopherol from mixtures of α-, γ- and δ-tocopherol. Another process for separating the tocopherol homologues is disclosed in U.S. Pat. No. 4,480,108. This process uses a nonaromatic saturated amine to selectively deacylate one of the tocopherol homologues. While this is an excellent process, the process requires a fairly expensive cyclic amine which requires recovery and ultimate disposal. Therefore, it would be an advance in the state of the art to provide a more inexpensive, simple and efficient process for separation of the various tocopherol homologues from mixtures of such homologues.

In accordance with the present invention, it has been discovered that methanol, ethanol and propanol readily deacylate the β-, γ- and δ-tocopheryl esters. However, the α-tocopheryl esters are relatively inert to such deacylation. Therefore, by merely reacting a mixture of tocopheryl ester homologues with a primary alcohol containing 1 to 3 carbon atoms can provide a mixture of δ-, β-, and γ-tocopherols with α-tocopheryl ester. The simple separation of the ester fraction from the tocopherol fraction by any of several methods (e.g., chromatography, ion exchange, distillation) leads to a separation of tocopherols and α-tocopheryl ester.

Generally, reacting the mixed tocopheryl acetates (α, β, γ, and δ) with methanol, ethanol, or propanol which, for example, is also a suitable solvent, for a period of at least 30 minutes at a temperature of about 180° C. to about 250° C., preferably 190° to 210° C., leads to rapid deacylation of δ-tocopheryl, β- and γ-tocopheryl but not the α-tocopheryl ester such as the acetate. In order to carry out the reaction it is, of course, necessary to carry out the reaction in a closed pressure vessel because of the boiling point of the alcohols. Since the polarity of the acetate is significantly different from that of the free tocopherol, this can allow the efficient chromatographic isolation of α-tocopheryl acetate. In addition, if one begins with a mixture that is mainly γ- and α-tocopheryl acetates (such as is obtained after removal of δ-tocopherol from natural tocopherol concentrates with basic ion-exchange resins followed by acetylation with acetic anhydride) methanol deacylation of γ-acetate 3 allows simple chromatographic purification of γ-tocopherol, 3b.

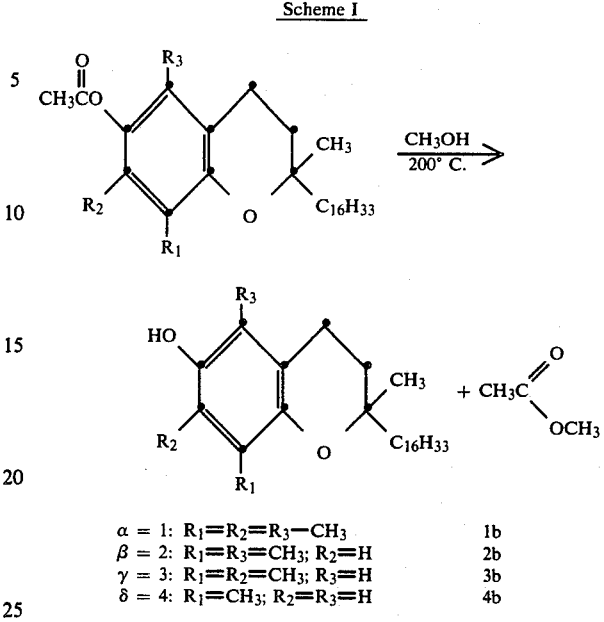

Scheme I

α = 1: $R_1=R_2=R_3=CH_3$    1b
β = 2: $R_1=R_3=CH_3$; $R_2=H$    2b
γ = 3: $R_1=R_2=CH_3$; $R_3=H$    3b
δ = 4: $R_1=CH_3$; $R_2=R_3=H$    4b

The reaction rate is dependent on the reaction temperature, the particular alcohol used, and the amount of the particular alcohol being used. Lowering the reaction temperatures below 180° C. extends the reaction period to more than eight hours for adequate deacylation. Also, methanol reacts faster than ethanol, and ethanol reacts faster than n-propanol, while secondary aliphatic alcohols such as isopropanol react too slowly to be useful. The amount of alcohol used is at least 1 mole to 1 mole tocopheryl acetate mixture, preferably with a large molar excess.

This invention can be further illustrated by the following examples of preferred embodiments thereof, although it will be understood that these examples are included merely for purposes of illustration and are not intended to limit the scope of the invention unless otherwise specifically indicated.

EXAMPLE 1

About 30 g of a refined soybean oil distillate concentrate containing a mixture of tocopheryl acetates (7.5%, α; 0.77%, β; 21.15%, γ; 7.78%, δ) was dissolved in 10 ml methanol and heated at 200° C. for two hours. The mixture was cooled and the solvent removed by distillation. A GPCL analysis showed all of the δ-acetate, 89% of the γ-acetate and only 13% of the α-acetate had been converted to free tocopherols. The mixture can then be separated according to procedures well known in the art. The tocopherol ester fraction (now mostly α-tocopheryl acetate) can be converted to α-tocopherol by simple saponification.

EXAMPLE 2

A solution of 1.0 g of α-tocopheryl acetate and 1.0 g of δ-tocopheryl acetate in 35 ml of methanol and 100 ml of isooctane was heated at 200° C. for four hours. Solvent was removed by distillation. A GLPC analysis showed that all of the δ-tocopheryl acetate had been converted to δ-tocopherol but that the α-tocopheryl acetate remained essentially unconverted. The mixture can then be separated according to procedures known in the art.

EXAMPLE 3

A 6-gram sample of a mixture of tocopheryl acetates used in Example 1 and 35 ml of isopropanol was heated at 200° for four hours. The solvent was removed by distillation. A GLPC analysis of the product showed none of the α-ester had deacylated and only 24% of the δ- and 12% of the γ-esters had deacylated.

The invention has been described in detail with particular reference to preferred embodiments thereof, but it will be understood that variations and modifications can be effected within the spirit and scope of the invention.

I claim:

1. A process for separating tocopherol homologues which comprises reacting a mixed α-, β-, γ, and δ-tocopheryl ester mixture with at least one alcohol of the group consisting of methanol, ethanol and propanol at a temperature of about 180° C. to about 250° C. to deacylate tocopheryl esters other than the α-tocopheryl esters and separating the α-tocopherol ester from the deacylated homologues.

2. A process for isolating α-tocopheryl esters from the β, γ, and δ-tocopheryl ester homologues according to claim 1 which comprises reacting the mixture of esters with at least one mole of at least one alcohol of the group consisting of methanol, ethanol and propanol at a temperature of about 180° C. to about 250° C. to deacylate the β-, γ, and δ-tocopheryl esters and thereafter separating the α-tocopheryl ester fraction from the tocopherol homologue fraction.

3. A process for forming a mixture of β-, γ, and δ-tocopherol homologues and α-tocopheryl ester which comprises reacting a mixture of α-, β-, γ, and δ-tocopheryl esters with at least one alcohol of the group consisting of methanol, ethanol and n-propanol at a temperature of about 180° C. to about 250° C. to deacylate tocopheryl esters other than the α-tocopheryl ester.

4. A process according to claim 1 wherein said alcohol is methanol.

5. A process according to claim 1 wherein said alcohol is ethanol.

6. A process according to claim 1 wherein said alcohol is propanol.

* * * * *